(12) United States Patent
Poland et al.

(10) Patent No.: US 7,622,120 B2
(45) Date of Patent: Nov. 24, 2009

(54) PEPTIDE ORIGINATING FROM VACCINIA VIRUS

(75) Inventors: Gregory A. Poland, Rochester, MN (US); Inna G. Ovsyannikova, Rochester, MN (US); David C. Muddiman, Raleigh, NC (US); Kenneth L. Johnson, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 11/738,210

(22) Filed: Apr. 20, 2007

(65) Prior Publication Data

US 2007/0248625 A1 Oct. 25, 2007

Related U.S. Application Data

(60) Provisional application No. 60/793,984, filed on Apr. 21, 2006.

(51) Int. Cl.
*A61K 39/38* (2006.01)
*A61K 39/00* (2006.01)
*A61K 39/12* (2006.01)
*A61K 39/275* (2006.01)
*C07K 14/00* (2006.01)
*A61K 39/155* (2006.01)

(52) U.S. Cl. ............. 424/186.1; 424/232.1; 424/184.1; 424/185.1; 530/300

(58) Field of Classification Search .................. None
See application file for complete search history.

(56) References Cited

OTHER PUBLICATIONS

Berhanu et al., Vaccination of BALB/c Mice with *Escherichia coli*-Expressed Vaccinia Virus Proteins A27L, B5R, and D8L Protects Mice from Lethal Vaccinia Virus Challenge, 2008, Journal of Virology, vol. 82, No. 7, pp. 3517-3529.*
CDC Smallpox Report, Published Mar. 31, 2003.*
Genbank Accession # AAG37665, published Jul. 30, 2002.*
Rodriguez-Ortega et al., Characterization and identification of vaccine candidate proteins through analysis of the group A Streptococcus surface proteome, Nature Biotechnology, Feb. 2006, 24(2), 191-7. Epublished Jan. 15, 2006.
Meiring et al., Stable isotope tagging of epitopes: a highly selective strategy for the identification of major histocompatibility complex class I-associated peptides induced upon viral infection, Molecular and Cellular Proteomics, May 2006, 5(5), 902-13. Epublished Jan. 23, 2006.
Meiring et al., Mass tag-assisted identification of naturally processed HLA class II-presented meningococcal peptides recognized by CD4+ T lymphocytes, Journal of Immunology, May 1, 2005, 174(9), 5636-43.
Flyer at al, DC, Identification by mass spectrometry of CD8(+)-T-cell Mycobacterium tuberculosis epitopes within the Rv0341 gene product, Infection and Immunity, Jun. 2002, 70(6), 2926-32.
Van Els et al., A single naturally processed measles virus peptide fully dominates the HLA-A*0201-associated peptide display and is mutated at its anchor position in persistent viral strains, European Journal of Immunology, Apr. 2000, 30(4), 1172-81.
Herr et al., Identification of naturally processed and HLA-presented Epstein-Barr virus peptides recognized by CD4 (+) or CD8(+) T lymphocytes from human blood, Proceedings of the National Academy of Science U S A. , Oct. 12, 1999, 96(21), 12033-8.
Tsai et al., Purification and characterization of a naturally processed hepatitis B virus peptide recognized by CD8+ cytotoxic T lymphocytes, Journal of Clinical Investigation, Jan. 15, 1996, 97(2), 577-84.
Tsomides et al., Naturally processed viral peptides recognized by cytotoxic T lymphocytes on cells chronically infected by human immunodeficiency virus type 1, Journal of Experimental Medicine, Oct. 1, 1994 180(4), 1283-93.

* cited by examiner

*Primary Examiner*—Gary B Nickol
*Assistant Examiner*—Benjamin P Blumel
(74) *Attorney, Agent, or Firm*—Quarles & Brady LLP

(57) ABSTRACT

A vaccine for preventing or treating Orthopoxvirus infection that induces a protective or therapeutic immune response, wherein the vaccine comprises (1) an amino acid sequence of 20 amino acid or less (preferably 12 amino acid or less and most preferably 11 amino acid or less) of the formula $X_1$-SEQ ID NO:1-$X_2$, wherein $X_1$ and $X_2$ are peptides of 0-11 amino acid in length comprising either native or non-native amino acid sequences, (2) an antigen-presenting cell pulsed with the peptide, or (3) a cell sensitized in vitro to the peptide is disclosed.

7 Claims, 2 Drawing Sheets

PEPTIDE ORIGINATING FROM VACCINIA VIRUS

CROSS-REFERENCE TO RELATED APPLICATIONS

This application claims the benefit of U.S. Provisional Patent Application No. 60/793,984, filed Apr. 21, 2006, and incorporated by reference.

STATEMENT REGARDING FEDERALLY SPONSORED RESEARCH OR DEVELOPMENT

This invention was made with United States government support awarded by the following agency: NIH—Midwest GLRCE: AI057153-3 (Poland A. Gregory-PI) Sep. 1, 2003-Feb. 28/0. The United States government has certain rights in this invention.

BACKGROUND

Peptide-based vaccines use small peptide sequences derived from target proteins as epitopes to provoke an immune reaction. These vaccines are a result of an improved understanding of the molecular basis of epitope recognition, thereby permitting the development of rationally designed, epitope-specific vaccines based on motifs demonstrated to bind to human class I or class II major histocompatibility complex (MHC) molecules. Of particular interest has been the discovery of epitopes (peptides of eight to eleven amino acids) that are specifically recognized by T cells for prophylaxis and treatment of infectious diseases.

Peptide-based vaccines offer several advantages over conventional vaccines for treating and preventing infectious diseases. For one, peptide-based vaccines are safer because they lack an infectious potential. In addition, peptide-based vaccines have a relatively long shelf-life because they are chemically stable and can be predictably, rapidly, and inexpensively manufactured. Furthermore, peptide-based vaccines allow one to target an immune response to specific epitopes that are neither suppressive nor hazardous for the host. Lastly, peptide-based vaccines allow for the possibility of preparing a multi-pathogen vaccine.

One particular infectious disease in which peptide-based vaccines have considerable potential in treating and preventing is viral infections, including Orthopoxvirus infections such as smallpox. Even though the World Health Organization declared that smallpox from naturally occurring Variola virus was eradicated in 1980, it is still a potential threat because of bioterrorism.

Peptide-based vaccines are particularly promising with T cells. T cells are responsible for cellular-mediated immunity, which exist in adaptive immune systems. There are two subsets of T cells, CD4$^+$T cells and CD8$^+$T cells. Of particular interest are CD8$^+$T cells, known as cytotoxic T lymphocytes (CTLs), because they kill other infected cells and secreted antiviral cytokines. Unlike antibodies produced by B cells, receptors on CTLs only recognize short, yet contiguous, sequences on foreign antigens (epitope) complexed with class I MHC molecules on the surface of a cell. CTLs are important in immunity against cytosolic pathogens, especially viruses.

Limitations in identifying class I MHC molecules include the difficulty in detecting pathogen-derived peptides eluted from class I MHC complexes and the lack of knowledge regarding MHC class I presentation of viral peptides. Fortunately, the rapid characterization of defined peptides that are critical to viral immunity, including smallpox, has been significantly enhanced by mass spectrometry (MS), which provides peptide sequence information at the femtomole level of sensitivity.

Although direct sequencing of naturally processed peptides bound to class I MHC molecules by liquid chromatography mass spectrometry (LC-MS) is established, identification of pathogen-derived peptides presents a formidable challenge due to the diverse range of low abundance peptides presented by class I MHC molecules. Strategies to reduce the complexity of the mixture prior to introduction into the mass spectrometer have often relied on multiple steps of reversed phase (RP) liquid chromatography. However, this approach does not effectively increase the peak capacity because the separation mechanisms of each RP chromatography step are not orthogonal.

Accordingly, there is a renewed need for prophylaxis, therapeutics, and for diagnostics for Orthopoxvirus infections, particularly those that are based on the isolation of naturally processed viral peptides from class I MHC antigens.

SUMMARY

In one embodiment, the present invention is an isolated peptide, wherein the peptide comprises $X_1$-SEQ ID NO:1-$X_2$, wherein $X_1$ and $X_2$ are amino acid sequences of 0-11 amino acids in length comprising either native vaccinia or non-native sequences. In one specific embodiment, $X_1$ and $X_2$ comprise naturally occurring contiguous thymidylate kinase sequence. In four other embodiments, the peptide (1) comprises 20 amino acids or less, (2) comprises 12 amino acids or less, (3) is chemically synthesized, and/or (4) comprises either $X_1$ or $X_2$ equal to zero.

In one embodiment, the present invention is a vaccine for preventing or treating Orthopoxvirus infection that induces a protective therapeutic immune response, wherein the vaccine comprises the peptide $X_1$-SEQ ID NO:1-$X_2$, wherein $X_1$ and $X_2$ are amino acid sequences of 0-11 amino acids in length comprising either native vaccinia or non-native sequences.

In another embodiment, the invention is a vaccine for preventing or treating Orthopoxvirus infection that induces a protective or therapeutic immune response, wherein the vaccine is selected from the group consisting of (1) a peptide of 20 amino acid or less of the formula $X_1$-SEQ ID NO:1-$X_2$, wherein $X_1$ and $X_2$ are amino acid sequences of 0-11 amino acid in length comprising either native or non-native amino acid sequences, (2) an antigen-presenting cell pulsed with the peptide, and (3) a cell sensitized in vitro to the peptide. In one specific embodiment, the vaccine additionally comprises additional MHC Class I or Class II vaccinia virus peptides. In another embodiment, the vaccine comprises an adjuvant.

In another embodiment, the invention is an antibody specific for SEQ ID NO:1. In one specific embodiment, the antibody is a monoclonal antibody. In another specific embodiment, the antibody suppresses, neutralizes or kills virus containing SEQ ID NO:1.

In another embodiment, the invention is a method of diagnosing an Orthopoxvirus infection or the presence of immunity to a virus comprising the steps of examining a human or animal patient for SEQ ID NO:1 or antibodies to SEQ ID NO:1. In one specific embodiment, the SEQ ID NO: 1 or antibodies to SEQ ID NO:1 are attached to a microarray.

In another specific embodiment, the method is used to diagnose a smallpox infection. In still another specific embodiment, a mass spectrometry assay is used to detect the presence of SEQ ID NO:1.

In another embodiment, the invention is a nucleic acid sequence coding for the peptide comprising $X_1$-SEQ ID NO:1-$X_2$, wherein $X_1$ and $X_2$ are peptides of 0-11 amino acids in length comprising either native vaccinia or non-native sequences.

DETAILED DESCRIPTION OF PREFERRED EMBODIMENTS

Figure 1:
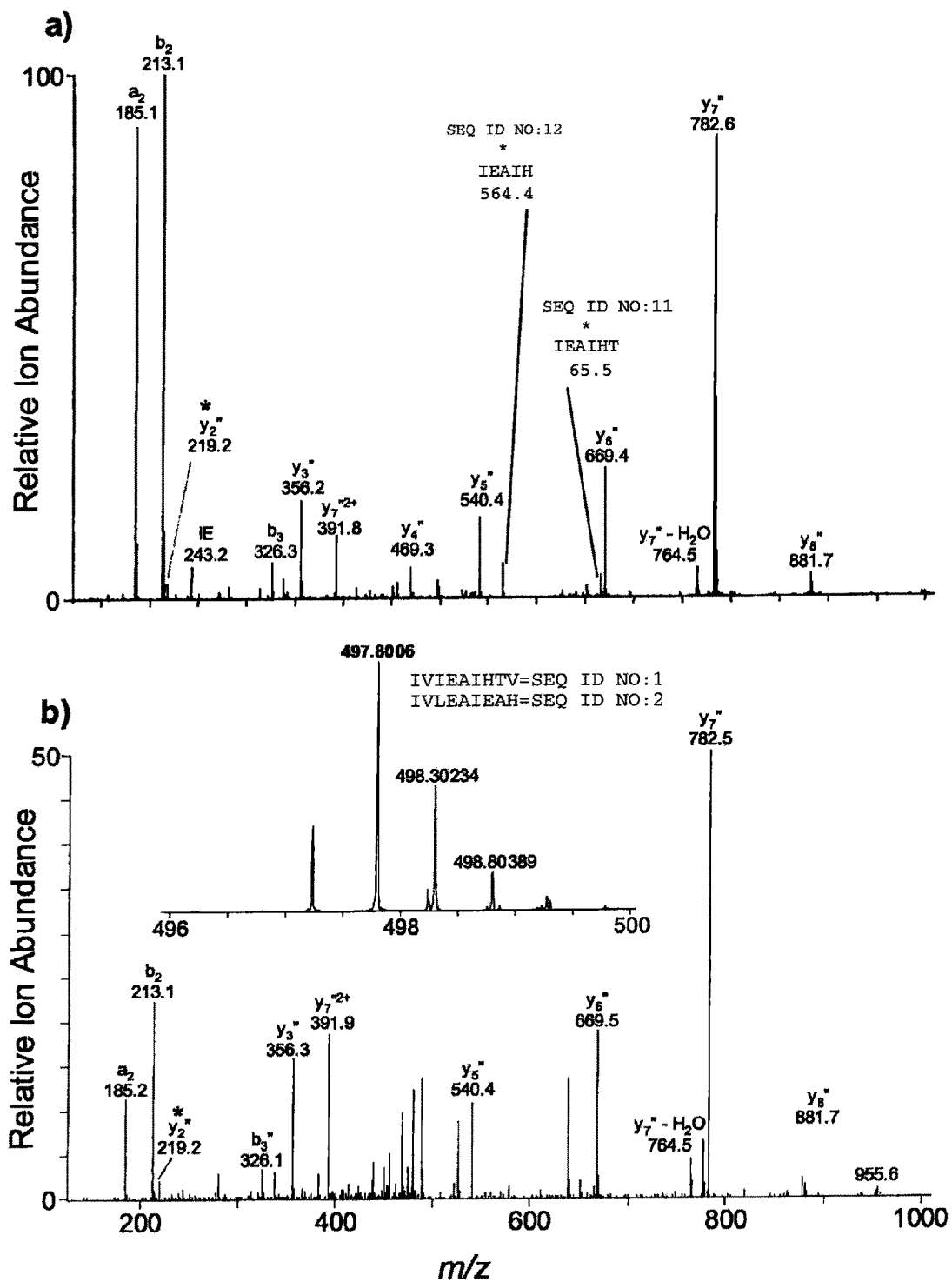
FIG. 1: MS/MS and FTICR-MS data for a class I peptide identified as IVIEAIHTV (SEQ ID NO: 1), from thymidylate kinase of vaccinia. a) QToF II MS/MS spectrum. b) MS/MS spectrum from a linear ion trap-FTICR hybrid instrument (LTQ-FT). MS/MS ions marked with an asterisk (*) denote fragmentation products that distinguish the sequence IVIEAIHTV (SEQ ID NO: 1) from IVLEAIEAH (SEQ ID NO: 2). All other labeled fragment ions support both sequences. The inset of b) shows the FT-ICR accurate mass spectrum of the doubly-charged precursor ion that conclusively identifies the correct sequence as IVIEAIHTV (SEQ ID NO: 1).

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

As used herein, an epitope is defined as that part of an antigen that is recognized by the immune system and targeted by antibodies, CTLs or both.

Disclosed herein are methods and compositions incorporating a peptide fragment isolated from a naturally processed and presented class I peptide originating from Vaccinia virus, a member of the Orthopoxvirus family originally isolated from cowpox and the viral agent used in the smallpox vaccine in the United States.

In one aspect, the invention is an isolated peptide comprising the amino acid sequence $X_1$-IVIEAIHTV-$X_2$ (SEQ ID NO:1; amino acids 187-195 of thymidylate kinase of Vaccinia virus), wherein $X_1$ and $X_2$ are peptides of 0-11 amino acids in length comprising either native vaccinia or non-native sequences. Preferably, the amino acid sequence is the naturally occurring contiguous thymidylate kinase sequence. Preferably, the peptide is 20 amino acids or less, more preferably 12 amino acids or less, and the most preferably 11 amino acids or less.

It appears that among the most important pocket anchors are those at position 2 and 9 of the SEQ ID NO:1. One may make conservative substitutions or substitutions without functional effect in residues other than 2 and 9 and still have an equivalent of SEQ ID NO:1.

The phrase "isolated" refers to material which is substantially or essentially free from components which normally accompany the material as it is found in its native state. Thus, isolated peptides in accordance with the invention preferably do not contain materials normally associated with the peptides in their in situ environment An "isolated" epitope refers to an epitope that does not include the whole sequence of the antigen or polypeptide from which the epitope was derived. Typically the "isolated" epitope does not have attached thereto additional amino acids that result in a sequence that has 100% identity with a native sequence. The native sequence can be a sequence such as a thymidylate kinase from which the epitope is derived.

The peptide structure $X_1$-SEQ ID NO:1-$X_2$ can also be conjugated to or mixed with other agent to improve overall efficacy. For example, the vaccine may be coupled to one or more agents, such as a lipophillic tag, to allow for passive diffusion into a cell.

In some embodiments, $X_1$-SEQ ID NO:1-$X_2$ is synthesized by methods known to one skilled in the art of making peptides. Of course, other methods in the art would be appropriate. A variety of methods are available now and in the future to obtain the peptides of interest. One method is simple chemical synthesis of the peptide. Another method would be inserting the polynucleotide sequence for the peptide of interest into a plasmid or other vector that is then delivered to the host and induced to transcribe the polynucleotide into the peptide of interest. Alternatively, one would insert a polynucleotide sequence for a larger peptide into a host if it were certain that the larger peptide would then be processed into the smaller peptide or a functionally equivalent variant.

In some embodiments, the peptide is combined with a pharmaceutically acceptable carrier or pharmaceutical excipient. "Pharmaceutically acceptable" refers to a generally non-toxic, inert, and/or physiologically compatible composition. A "pharmaceutical excipient" comprises a material such as an adjuvant, a carrier, pH-adjusting and buffering agents, tonicity adjusting agents, wetting agents, preservative, and the like.

In alternative embodiments, peptides of the invention can be linked as a polyepitopic peptide or as a minigene that encodes a monoepitopic or polyepitopic peptide.

In a second aspect, the invention is a peptide-based vaccine comprising $X_1$-SEQ ID NO:1-$X_2$. Preferably, such a vaccine would be based on a combination of naturally processed and presented Vaccinia virus peptides. For examples of peptide vaccines with other viral targets, see Belyakov, I M et al., *Proc. Natl. Acad. Sci. U.S.A.*, Vol. 95, Issue 4, 1709-1714, Feb. 17, 1998 and Jackson, D C et al., *Proc. Natl. Acad. Sci. U.S.A.*, 2004 Oct. 26; 101(43): 15440-5.

In one embodiment, the vaccine is a vaccine for preventing or treating Orthopoxvirus infection that induces a protective or therapeutic immune response, wherein the vaccine comprises (1) a peptide of 20 amino acid or less (preferably 12 amino acid or less and most preferably 11 amino acid or less) of the formula $X_1$-SEQ ID NO:1-$X_2$, wherein $X_1$ and $X_2$ are peptides of 0-11 amino acid in length comprising either native or non-native amino acid sequences, (2) an antigen-presenting cell pulsed with the peptide, or (3) a cell sensitized in vitro to the peptide. Preferably, the vaccine is directed to any Orthopoxvirus. More preferably, the vaccine is directed to monkeypox, cowpox and camelpox. Most preferably, the vaccine is directed to vaccina or variola major or minor. Examples of vaccinia-specific single peptide vaccines are: Snyder, J T, et al., *J. Virol.*, 2004 July;78(13):7052-60, and Drexler, I, et al., *Proc. Natl. Acad. Sci. U.S.A.*, 2003 Jan. 7; 100 (1):217-22. One of skill in the art would wish to adapt various features of these vaccines to the present invention.

While there is no clear-cut hierarchy of immunodominance with the currently identified CTL epitopes, there are hints that certain proteins/peptides may be more immunodominant than others. Certain proteins which contain multiple CTL epitopes restricted by various HLA-class I alleles (A10L-7 epitopes; D1R, D5R-5 epitopes,; A3L, B8R, F12L-4 epitopes, etc.). Other reports have shown multiple individuals responsive to the same peptide. For example, the following discuss immunodominance: Kennedy, R, et al., *Rev. Med. Virol.*, 2007 March-April;17(2):93-113; Terajima, M, et al., *Hum. Immunol.*, 2006 July;67(7):512-20; and Moutaftsi, M, et al., *Nat. Biotechnol.*, 2006 July;24(7):817-9.

An "antigen-presenting cell" is a specialized cell that express class I and/or class II MHC proteins on its cell surface. Short peptides associate non-covalently with the surface class I and class II MHC proteins which are then detected by other T cells such as T helper cells (HTL or helper T lymphocytes). The major types of antigen presenting cells include, macrophages, B cells, and dendritic cells. A "protective immune response" or "therapeutic immune response" refers to a CTL and/or an HTL response to an antigen derived from an infectious agent or a tumor antigen, which prevents or at least partially arrests disease symptoms or progression. The immune response may also include an antibody response which has been facilitated by the co-stimulation of helper T cells.

With respect to a peptide-based vaccine, SEQ ID NO:1 is highly conserved among all other Orthopoxvirus families This suggests that if human CTLs recognize SEQ ID NO:1 for preventing: 1) vaccinia infection; 2) variola infection; and 3) other Orthopoxvirus infections, such as cowpox, monkeypox, and camelpox.

Developing peptide-based vaccines consisting of synthetic peptides representing T cell epitopes is a promising strategy. Accordingly, it is possible to develop a peptide-based smallpox vaccine based on a combination of naturally processed and presented MHC class I and/or class II Vaccinia virus peptides. For example, the following discuss naturally processed and presented vaccinia peptides useful in the present invention: Jing, L, et al., *J. Immunol.,* 2005 Dec. 1;175(11): 7550-0 and Yoder, J D, et al., *Virol. J.,* 2006 Mar. 1;3:10.

The steps in the development of a peptide-based smallpox vaccine would include selection of appropriate immunogenic peptides that can elicit cellular immunity, particularly highly conserved peptides, optimization of peptide dose and/or inclusion of adjuvants, and administration and delivery methods. For examples of peptide-based vaccines and peptide immunization in humans, see Vitiello A, et al., *J Clin. Invest.* 1995 January; 95(1):341-9 and Hsu S C, et al., *J Gen. Virol.,* 1999 June; 80 (Pt. 6):1401-5.

In a third aspect, the invention is polyclonal or monoclonal antibodies to Vaccinia virus peptides, preferably specific to SEQ ID NO:1 and preferably made by standard means. For example see Brander C, et al., *Clin. Exp. Immunol.* 1996 July; 105(1): 18-25 and Walker E B, et al., *Clin. Cancer Res.* 2004 Jan. 15; 10(2):668-80.

In some embodiments, the antibodies are used as a therapeutic in a subject exposed to Orthopoxviruses. In preferred embodiments, antibodies against SEQ ID NO:1 supress, neutralize or kill Variola virus that contain SEQ ID NO:1. $CD8^+$T cells raised by immunization and/or re-immunization to SEQ ID NO:1 will most likely recognize cells infected with Vaccinia virus or an Orthopoxvirus. As examples of other therapeutics, vaccinia immunoglobulin, rabies immunoglobulin, hepatitis B immunoglobulin, varicella immunoglobulin and tetanus immunoglobulin are all successfully used as therapeutics. HERCEPTIN(TRASTUZUMAB) is used in breast cancer treatment; BEVACIZUMAB is used for colorectal cancer; and MATUZUMAB is used for ovarian and peritoneal malignancies. See Simonds, H M, et al., *Expert Opin. Biol. Ther.,* 2007 April; 7(4):487-91, Shih, T, et al., *Clin. Ther.,* 2006 November; 28(11):1779-802, and Seiden, M V, et al., *Gynecol Oncol.* 2007 March; 104(3):727-31 for other monoclonal therapies. Therapies for immune modulation/infections/autoimmune disorders, such as Crohn's disease, RSV infection, allergic rhinitis, GVHD, are illustrated by Mascelli, M A, et al., *J. Clin. Pharmacol.,* 2007 Mar. 22.

In a fourth aspect, the invention is a diagnostic aid or a laboratory assay for detecting the presence of Orthopoxviruses that comprise SEQ ID NO:1. Alternatively, one Shih, T, et al., *Clin. Ther.,* 2006 Nov; 28(11): 1779-802, and Seiden, M V, et al., *Gynecol Oncol.* 2007 March; 104(3): 727-31 for other monoclonal therapies. Therapies for immune modulation/infections/autoimmune disorders, such as Crohn's disease, RSV infection, allergic rhinitis, GVHD, are illustrated by Mascelli, M A, et al., *J. Clin. Pharmacol.,* 2007 Mar. 22.

In a fourth aspect, the invention is a diagnostic aid or a laboratory assay for detecting the presence of Orthopoxviruses that comprise SEQ ID NO:1. Alternatively, one may determine immunity to smallpox or related Orthopoxviruses. Since SEQ ID NO:1 is highly conserved among the Orthopoxviruses and is immunogenic, it can be used in diagnostic assays to detect the presence of any virus that contains SEQ ID NO:1.

For example, microarrays can be produced with antibodies to SEQ ID NO:1. When a clinical specimen, such as blood, urine, CSF or tissue containing an Orthopoxvirus with SEQ ID NO:1, antibody fixed to the microarray will bind the peptide and indicate the presence of virus.

Similarly, assays using the converse method can be produced. For example, SEQ ID NO:1 can be fixed to a microarray plate. If a clinical specimen contains antibody to SEQ ID NO:1 and is placed on the microarray plate, it will bind to SEQ ID NO:1 (acting as an antigen) and indicate the presence of such antibody (appear as a positive). Other diagnostic assays can also be developed such as highly sensitive mass spectrometry assays that could detect the presence of SEQ ID NO:1—hence indicating the presence of a virus with SEQ ID NO:1. Yet other assays could bind SEQ ID NO:1 and a reporter protein to beads, which when mixed with a clinical specimen, if antibody is present to SEQ ID NO:1, so indicate the presence of antibody (immunity).

In a fifth aspect, the invention is a nucleic acid sequence which codes for $X_1$-SEQ ID NO:1-$X_2$ or variants thereof and other nucleic acid sequences that hybridize to a sequence consisting of the above-described nucleotide sequences under high stringency conditions. The term "stringent conditions" as used herein refers to parameters with which the art is familiar. For example, nucleic acid hybridization parameters may be found in references which compile such methods, e.g., Sambrook, et al., "Molecular cloning: a laboratory manual, " Cold Spring Harbor Laboratory Press, Cold Spring Harbor, N.Y. (2nd ed. 1989) or Ausubel, et al., "Current protocols in molecular biology," John Wiley & Sons, Inc., New York (1995).

The previously described embodiments have many advantages, including a first advantage that the safety problems and contraindications present for any live viral vaccine are eliminated.

It is a second advantage in that antibodies against Orthopoxviruses would allow a new method of treatment for a subject with a current Variola virus, Vaccinia virus, or other Orthopoxvirus infections.

These and other features, aspects and advantages of the present invention will become better understood from the description that follows. The description of preferred embodiments is not intended to limit the invention to cover all modifications, equivalents and alternatives. Reference should therefore be made to the claims herein for interpreting the scope of the invention.

EXAMPLE

Example 1

Isolation of Vaccinia Epitope

Johnson K, et al., "Accurate mass precursor ion data and tandem mass spectrometry identify a class I human antigen A*0201-presented peptide originating from vaccinia virus," J. Am. Soc. Mass. Spectrom. 16:1812-1817 (2005), incorporated herein by reference as if set forth in its entirety, is an academic publication by the inventors describing their work using accurate mass precursor ion data generated on a hybrid linear-ion trap-Fourier transform ion cyclotron resonance mass spectrometer to augment tandem mass spectrometerty data generated on two different instrument types. The experiments described therein and below identified a naturally processed peptide (SEQ ID NO:1) presented by a Class I human leukocyte antigen allele (HLA-A*0201) isolated from B-cells infected by live Vaccinia virus.

Introduction

Advances in mass spectrometry instrumentation and associated analytical methods have led to unprecedented growth in the application of mass spectrometry to research in the life sciences. The development of electrospray ionization (Fenn, J. B., et al. *Science* 1989, 246, 64-71), advances in miniaturized chromatography (Moseley, M. A., et al. *Anal Chem* 1991, 63, 1467-1473, Emmett, M. R., et al. *Journal of the American Society for MassSpectrometry* 1994, 5, 605-613), tandem mass spectrometry of peptides (Hunt, D. F., et al. *Science* 1992, 255, 1261-1263), and multi-dimensional LC separations (Link, A. J., et al. *Nat Biotechnol* 1999, 17, 676-682, Washburn, M. P., et al.; *Nat Biotechnol* 2001, 19, 242-247) have successively enabled other researchers in the application of mass spectrometry to their respective areas of research. As an example, we have employed the use of multi-dimensional LC together with automated acquisition of MS/MS data for the identification of self-peptides and peptides originating from measles virus proteins that were displayed by the HLA class II system from cultured B cells infected with measles virus. (Ovsyannikova, I. G., et al. *Virology* 2003, 312, 495-506, Ovsyannikova, I. G., et al. *J Virol* 2004, 78, 42-51, Ovsyannikova, I. G., et al. *J Immunol Methods* 2005, 297, 153-167.)

Most recently, the development and commercialization of hybrid mass spectrometers incorporating FT-ICR analyzers, with high resolving power and high mass accuracy offer additional opportunities to enhance the utility of mass spectrometry in biological research. (Hunt, D. F., et al. *Anal Chem* 1985, 57, 2728-2733, Syka, J. E., et al. *J Proteome Res* 2004, 3, 621-626.) As a result, the effectiveness of combining accurate mass data from the precursor ion with tandem mass spectrometry data has been reported. (Smith, R. D., et al. *Proteomics* 2002, 2, 513-523, Olsen, J. V., et al. *Mol Cell Proteomics* 2004, 3, 608-614.)

This application note describes an example where the high mass accuracy of a hybrid 2D-ion trap-FTICR-MS instrument combined with tandem mass spectrometry data enables confident sequence assignment of a naturally processed and presented class I peptide originating from vaccinia, the viral agent used in the smallpox vaccine, and distinguishing it from a similar sequence from the human protein phospholipase Cβ3.

T helper cells play an important role in orchestrating the effector function of cytotoxic T lymphocytes (CTL) in immunity against Orthopoxvirus infection. Only a few vaccinia virus class I peptides and HLA-A*0201-restricted CD8+T cells are described in the literature (Drexler, I., et al. *Proc Natl Acad Sci USA* 2003, 100, 217-222, Snyder, J. T., et al. *J Virol* 2004, 78, 7052-7060, Mathew, A., et al. *J Immunol* 2005, 174, 2212-2219); however, no naturally processed and presented vaccinia virus T cell epitopes have been identified. One major obstacle is the size of the virus. Vaccinia is a large, double-stranded virus, which replicates in the nucleus of infected cells, with an ~200-kbp DNA genome, encoding more than 230 open reading frames and expressing more than 200 proteins (Moss, B. *Comprehensive Virology* 1974, 3, 405-474, Goebel, S. J., et al. *Virology* 1990, 179, 247-266, 517-263). In addition, information about immunodominant Orthopoxvirus antigens and epitope specificities of virus-specific CTL responses is still lacking (Drexler, I., et al. *Proc Natl Acad Sci USA* 2003, 100, 217-222). Therefore, the role of specific peptides presented in the context of HLA molecules to T cells can be considered as one of the most important fundamental questions for understanding immune responses to vaccinia and other Orthopoxviruses. In this study, we report a new naturally processed and HLA-A*0201-presented peptide epitope derived from vaccinia virus, that is encoded by the vaccinia virus gene thymidylate kinase and is highly conserved in vaccinia, variola and other Orthopoxviruses.

Experimental

Vaccinia Infection of B Cells

The New York City Board of Health (NYCBH, Dryvax™) vaccine-strain of vaccinia virus was cultured in HeLa cells in Dulbecco's modified Eagle's medium, supplemented with 5% fetal calf serum (virus stocks of 6.3 ×$10^8$ pfu/mL). An established EBV-transformed human HLA-A*0201 homozygous cell line, Priess (ECACC, cell ID No. 11277) was used for this study. Cells were infected with live vaccinia virus at a multiplicity of infection (moi) of 0.1 pfu/cell for 2 hours and maintained for 24 hours at 37° C. The uninfected and vaccinia-infected cells were used for obtaining cell lysates for purification of HLA-A2 molecules. Equal-sized batches of uninfected and vaccinia-infected cells were prepared, washed in phosphate-buffered saline, pelleted, and stored at −80° C. for isolation of HLA-A*0201 molecules and HLA-A*0201-bound peptides. Infection of cells with vaccinia was confirmed by flow cytometry using a polyclonal anti-vaccinia antibody specific for vaccinia proteins (Fitzgerald Industries International, Inc., Concord, Mass.), followed by a fluorescein isothiocyanate (FITC)-conjugated secondary antibody (data not shown).

Production of HLA-A2 Monoclonal Antibodies (mAb) and Construction of Immuno Affinity Column The PA2.1 hybridoma (ATCC, Manassas, Va.) was the source of HLA-A2-reactive mAb. PA2.1 hybridoma cells (1 x $10^5$/ml) were cultured for 2-3 days in modified Dulbecco's medium. The hybridoma supernatants were collected, and IgG antibodies were purified using a protein G-Sepharose fast flow column (Pharmacia, Peapack, N.J.). Immuno affinity columns were constructed using CNBr-activated Sepharose 4B (Sigma-Aldrich Corp., St. Louis, Mo.), covalently coupled to the purified HLA-A2 specific mAb (PA2.1, IgG1). For coupling, 20 mM dimethyl pimelimidate dihydrochloride (DMP) was used. Briefly, 7.5 mL of protein A-Sepharose were washed in 20 mL of 100 mM borate buffer, pH 8.2. Anti-HLA-A2 mAb (1.66 mg/mL) were diluted (15 mg to 30 mL) with 100 mM borate buffer, pH 8.2 and mixed with Sepharose for 30 minutes. After incubation, the Sepharose beads were spun at 1500 rpm and protein concentration of the supernatant was measured at 280 nm. Sepharose was poured into the column with sintered glass and was washed with 100 mM borate buffer, pH 8.2 and 200 mM triethanolamine, pH 8.2. Protein A-Sepharose then was coupled with fresh 20 mM DMP in 200 mM triethanolamine, pH 8.2 for 45 minutes by rocking and washing with 20 mL of 20 mM ethanolamine to block residues. Finally, Sepharose beads were washed with 100 mM borate buffer, pH 8.2 and equilibrated with 0.1% Nonidet-40, 10 mM Tris, pH 8.0.

Isolation of HL-A *0201-Associated Peptides

Uninfected and vaccinia-infected B cells were solubilized in 20 mM Tris, pH 8.0, 150 mM NaCl, 1% Chaps, 2mM PMSF, 100 µM iodoacetamide, aprotinin (5 ug/ml), leupeptin (10 ug/ml), pepstatin A (10 ug/ml), EDTA (3 ng/ml), and 0.2% sodium azide. After sample centrifugation at 100,000×g for 1 hour, supernatants were passed through an immunoaffinity column with HLA-A2.1-specific mAb (PA2.1) and protein A-Sepharose. HLA-A2 molecules were eluted from the column with 50 mM diethylamine, pH 11.5, 0.4% n-octyl-glucoside, 150 mM NaCl, and 0.02% $NaN_3$. Eluates were neutralized with 1M Tris, pH 6.8, and concentrated to 1 mg/ml by ultrafiltration (Centriprep 10, Amicon Corp., Danvers, Mass.). Acetic acid (14%) was used to dissociate any bound peptides from HLA-A2 molecules. The peptides were stored at −80° C. for later analysis by MS.

Desalting Peptides

Prior to 2D-LC, HLA class I peptides were desalted on a 1 mm i.d. by 10 mm long reversed phase cartridge (Peptide trap, Michrom BioResources, Inc. Auburn, Calif.), vacuum-concentrated to approximately 10 µL, and diluted with 15 µL water/acetonitrile/n-propanol/formic acid (98.5/1/0.5/0.2 by volume) also containing 0.0005% HFBA and 0.5 mM ammonium acetate.

Strong Cation Exchange Fractionation

Strong cation exchange (SCX) separations were performed using a 0.5 mm i.d. by 150 mm long Polysulfoethyl A column (Michrom BioResources, Inc.) at a flow rate of 25 µL/min. A gradient of 5 mM $KH_2PO_4$ (pH=3.1)/10% acetonitrile into 500 mM KCl (in the same phosphate/acetonitrile buffer) was used to fractionate peptides at one minute intervals. The mobile phase gradient started at 0% B with linear gradients to 20% B at 20 minutes, and 80% B at 30 minutes, followed by a 5 minute hold at 80% B, 5 minutes to return to 0% B and a 15 minute re-equilibration period (50 minute total method). A one meter length of 100 µm i.d. fused silica (8 µL volume, 0.33 min delay at 25 µL/min), was used to collect fractions via a Gilson FC 203B fraction collector.

Q-ToF II nLC-MS/MS Analyses

Initial automated nLC-MS/MS analyses were done on a Waters Q-Tof II and CapLC (Bedford, Mass.), using a 24 cm by 75 µm i. d. column packed in-house with Targa C18 (Higgins Analytical, Mountain View, Calif.). The autosampler loaded 10 µL aliquots of SCX fractions onto a 0.25 µL precolumn (Optimize Technologies, Oregon City, Oreg.), custom-packed with Michrom Magic C8, 5 µm, 300 Å (Michrom BioResources, Inc., Auburn, Calif.), that was inserted into a Cheminert 10-port switching valve (Valco Instruments Company, Inc., Houston, Tex.). Mobile phase A was water/acetonitrile/n-propanol/formic acid (98/1/1/0.2 by volume) and mobile phase B was acetonitrile/n-propanol/water/formic acid (80/10/10/0.2 by volume). A gradient from 3-50% B over 60 minutes was used at an approximate column flow of 0.2 µL/min. Pump C on the CapLC was used to transfer samples from the autosampler to the pre-column, using a 10 µL/min flow of water/acetonitrile/n-propanol/formic acid (98/1/1/0.2 by volume) that additionally contained 0.5 mM ammonium acetate. A 10 min transfer period (100 µL) was used to transfer sample and wash potassium salts from the peptides before switching the precolumn in-line with the nLC column and starting the reversed phase gradient.

Automated MS/MS measurements were performed on the three most intense doubly charged ions, using charge and m/z-dependent selection of collision energies. MS/MS spectra were searched against the NCBI nr database using MASCOT software, without enzyme constraints, using a precursor mass window of 0.3 mass units and a fragment ion mass window of 0.2 mass units (Perkins, D. N., et al. *Electrophoresis* 1999, 20, 3551-3567).

LTQ-FT nLC-MS/MS Analyses

Accurate mass nLC-FTICR-MS/MS measurements were performed on a ThermoFinnigan LTQ-FT (ThermoElectron, Bremen, Germany). A Michrom Paradigm LC (Michrom BioResources, Auburn, Calif.) plumbed with a 75 µm i.d. by 5 cm length Integrafrit column packed with ProteoPep II (New Objective, Woburn, Mass.) was used for the nLC separation. The sample was loaded on a 0.3 mm i.d. by 1 mm long precolumn packed with PepMap stationary phase (Dionex, Sunnyvale, Calif.).

The LTQ-FT was operated in a data dependant mode similar to that described in Olsen et al (Olsen, J. V., et al. *Mol Cell Proteomics* 2004, 3, 608-614) where a low resolving power (25000 FWHM at m/z 400) scan from m/z 375-1600 was acquired in the FT-ICR analyzer, followed by a high resolving power (rp=50000 FWHM at m/z 400) FT SIM scan over a 10 m/z window, with linear ion trap CID fragmentation and analysis on the top 3 most intense ions. (Olsen, J. V., et al. *Mol Cell Proteomics* 2004, 3, 608-614.) The ion population targets for the FT-ICR full scan and SIM scan were set at $3\times10^6$ and $1\times10^5$, respectively. The ion trap target population was set to $1\times10^5$ with 35% normalized collision energy.

Results and Discussion

Among the highly polymorphic human HLA class I molecules we chose the HLA-A*0201 allele, part of the HLA-A2 supertype, to search for CD8+ vaccinia virus T cell epitopes because the HLA-A2 supertype is extremely prevalent in the general population (~50%) (Ellis, J. M., et al. *Hum Immunol* 2000, 61, 334-340), its crystal structure has been solved (Bjorkman, P. J., et al. *Nature* 1987, 329, 506-512), and its ligand specificity has been examined in detail (Hunt, D. F., et al. *Science* 1992, 255, 1261-1263, Sidney, J., et al. *Hum Immunol* 2001, 62, 1200-1216, Kubo, R. T, et al. *J Immunol* 1994, 152, 3913-3924). We infected a class I HLA-A*0201 homozygous cell line with live vaccinia virus, and then searched for naturally processed and presented vaccinia virus-derived peptides.

Initial Mascot search results of MS/MS spectra generated by the Q-Tof II identified self peptides and peptides unique to bovine albumin, the latter attributed to the fetal calf serum used to culture the B-cells from which peptides were harvested. In addition, a MS/MS spectrum from SCX fraction 21 was tentatively identified as IVIEAIHTV (amino acid 187-195) from the protein thymidylate kinase of vaccinia virus, the immunogenic agent in the smallpox vaccine. Thymidylate kinase catalyzes a critical step in the biosynthesis of (deoxy) thymidine triphosphate and is indispensable for cell metabolism (Hughes, S. J. et al. *J Biol Chem* 1991, 266, 20103-20109). A BLAST search shows this sequence is conserved across a number of other poxvirus families.

FIG. 1A shows the spectrum obtained on the Q-ToF II. The MS/MS search results were not conclusive: despite the presence of a strong y-ion series, the MOWSE (Perkins, D. N., et al. *Electrophoresis* 1999, 20, 3551-3567) score for the top match was 46, with thresholds of 56 for similarity and 68 for identity. In addition, the top five matches all had the same score. In particular, the sequence IVLEAIAEH (SEQ ID NO: 2) from human phospholipase Cβ3 gave the same score and also equally accounted for the major fragment ions observed in the spectrum. Only three minor fragment ions, marked with asterisks (*) in FIG. 1, serve to differentiate the sequence of IVIEAIHTV (SEQ ID NO: 1) from IVLEAIAEH (SEQ ID NO: 2).

Table 1, below, lists the top ten sequence candidates, their chemical formula, MOWSE score, and m/z of their doubly charged ion. Candidate sequences 3-10 can be eliminated by the $y_3$ and $y_4$ ions, while the $y_5$ and higher y-ions are common to the first seven sequences. The first two candidate sequences differ in doubly charged mass by 0.018 mass units or 36 parts-per-million (36 ppm).

spectrum is searched using a precursor tolerance of 20 ppm, the only match is IVIEAIHTV (SEQ ID NO: 1) from vaccinia. It is noted that methylation of acidic residues followed by re-analysis would also serve to differentiate these two sequences at the cost of the additional derivitization procedure and its potential for further sample loss.

To frame this accurate mass result within the context of other identified peptides, we calculated the accurate mass deviations for six additional peptides. Five of six results ranged from <0.1 to 1.2 ppm mass error, consistent with results we have observed for tryptic peptides (data not shown). The sixth peptide's precursor mass was −15.7 ppm from the proposed sequence. The MOWSE score for this peptide was 40 (>40 for homology, >50 for identity). Inspection of the match results from this peptide showed that 6 of the 9 fragment ions with greater than 50% relative abundance

TABLE 1

Table 1. List of top ten most closely matched peptide sequences from a MASCOT search of an MS/MS spectrum from a Q-Tof II. Spectrum shown in FIG. 1A. The right hand column lists the deviation in mass of each of the sequences relative to an experimental result of 497.8006 obtained on a hybrid FT-ICR-MS instrument. Candidate sequences 3-10 can be more readily distinguished by the MS/MS data.

| sequence | Chemical Formula | MOWSE Score | $M_r$ | $[M + 2H^+]^{2+}$ | Δm/z (ppm) | SEQ ID NO: |
|---|---|---|---|---|---|---|
| IVIEAIHTV | C46H79N11O13 | 46.4 | 993.58588 | 497.80022 | −0.8 | 1 |
| IVLEAIAEH | C45H75N11O14 | 46.4 | 993.54950 | 497.78203 | −37.3 | 2 |
| LVLESPSHI | C45H75N11O14 | 46.4 | 993.54950 | 497.78203 | −37.3 | 3 |
| IVIESPIHS | C45H75N11O14 | 46.4 | 993.54950 | 497.78203 | −37.3 | 4 |
| IVLELACYA | C46H75N9O13S1 | 46.4 | 993.52051 | 497.76753 | −66.4 | 5 |
| LVLEVNNPP | C45H75N11O14 | 42.1 | 993.54950 | 497.78203 | −37.3 | 6 |
| LVLELLTHG | C46H79N11O13 | 42.1 | 993.58588 | 497.80022 | −0.8 | 7 |
| LVIDVELPP | C47H79N9O14 | 36.5 | 993.57465 | 497.79460 | −12.1 | 8 |
| LVLDVEIHG | C45H75N11O14 | 36.5 | 993.54950 | 497.78203 | −37.3 | 9 |
| LVLTLVLSH | C47H83N11O12 | 34.2 | 993.62227 | 497.81841 | 35.8 | 10 |

The remainder of SCX fraction 21 was analyzed on a ThermoFinnigan LTQ-FT. Results from this analysis on the LTQ-FT are shown in FIG. 1B, where first, the MS/MS spectrum from the LTQ-FT corroborates the MS/MS spectrum from the Q-Tof II shown in FIG. 1A. Secondly, the inset of FIG. 1B shows the precursor SIM scan from the FTICR analyzer that measured the doubly charged m/z as 497.8006. The column on the right side of Table 1 lists the deviations of this measured m/z from the theoretical m/z values for each of the top ten candidate sequences. The measured m/z is within 0.8 ppm of the calculated mass of IVIEAIHTV (SEQ ID NO: 1) from vaccinia, but is 37.3 ppm from the alternate sequence IVLEAIAEH (SEQ ID NO: 2) from phospholipase Cβ3. The seventh candidate sequence from Table 1, LVLELLTHG (SEQ ID NO: 7), also has the same chemical formula as IVIEAIHTV (SEQ ID NO: 1) however, the $Y_2$, $Y_3$, and $y_4$ ions from the tandem mass spectra serve to distinguish between the two sequences.

Since peptides presented by class I and II HLA molecules are not C-terminally constrained to Arg, Lys, or the protein C-terminus, many more candidate sequences will pass initial precursor ion mass filtering, to be subsequently scored on the basis of matching fragment ions. While accurate mass precursor ion data alone cannot definitively identify peptides, it greatly decreases the number of candidate sequences to be matched against the fragment ion data. When this MS/MS were not matched, strongly suggesting the proposed sequence was incorrect. The MOWSE score did not differentiate this false positive result from other results of similar MOWSE score, while the mass error of the precursor ion relative to the proposed sequence clearly differentiated this incorrect search result from the other peptides in this set.

Figure 2:
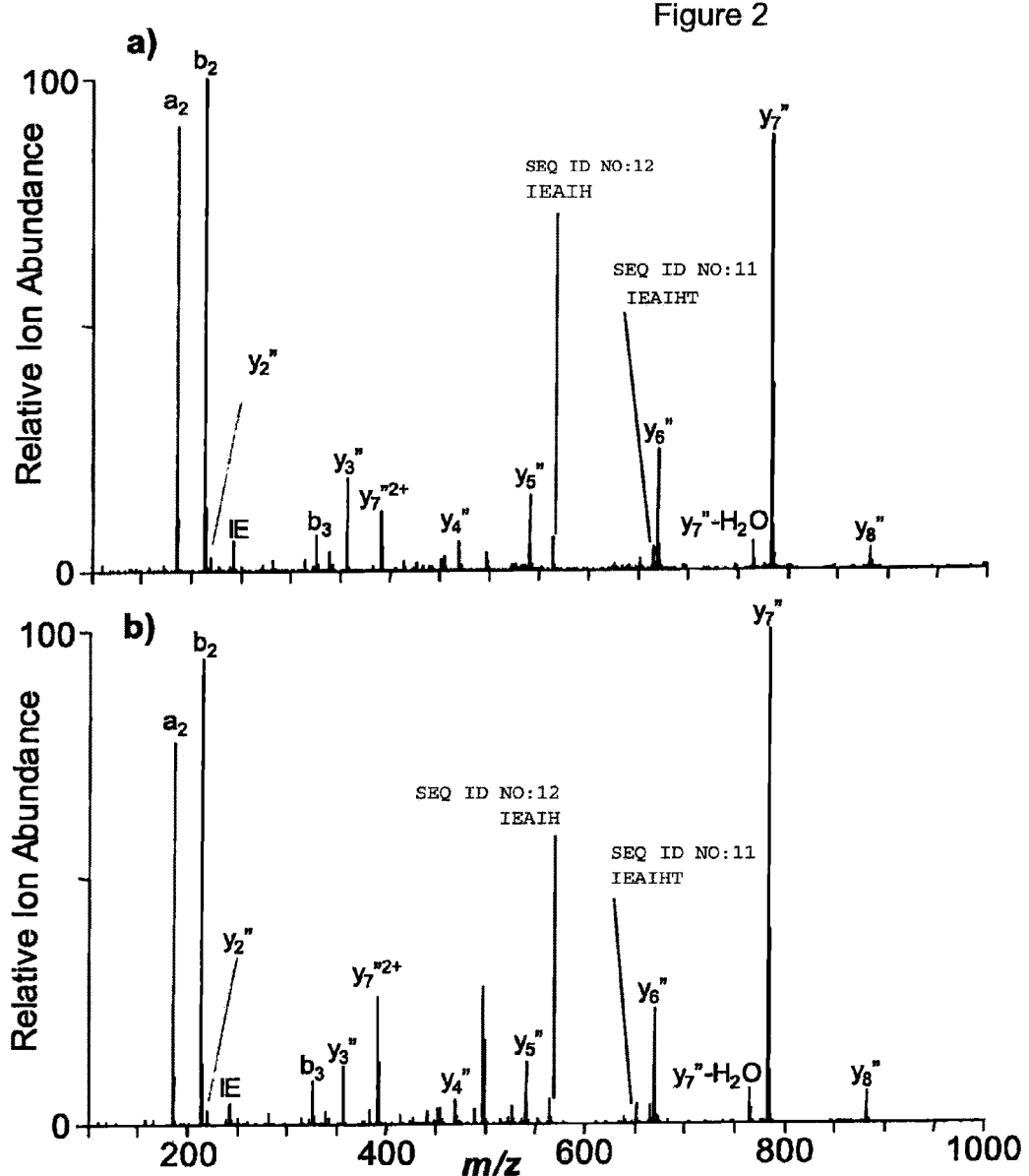
FIG. 2: MS/MS spectra from a) a naturally processed peptide isolated from vaccinia-infected B cells, and b) synthesized peptide with the sequence IVIEAIHTV (SEQ ID NO: 1), a sequence from thymidylate kinase that is conserved in a number of pox-viruses (listed in Table 2).

We also had the peptide synthesized, which was then analyzed by LC-MS/MS on our Q-Tof-2. FIG. 2 shows the original MS/MS spectrum from the naturally processed peptide (upper trace) compared to the MS/MS spectrum from the synthesized peptide, demonstrating the close agreement in fragmentation patterns and again confirming our identification.

When we looked at other Orthopoxviruses, we observed that this epitope, IVIEAIHTV (SEQ ID NO: 1), is highly conserved in vaccinia, variola, cowpox, monkeypox, and camelpox viruses (Table 2). This suggests that if human CTL will recognize this epitope, they will most likely recognize variola virus-infected cells as well. Since this epitope is endogenously processed and presented on HLA-A2 molecules of infected cells, one can hypothesize that CD8+T cells raised by immunization and re-stimulation with this peptide will most likely recognize cells infected with vaccinia virus. Thus, it may be possible to develop a new peptide-based smallpox vaccine based upon a combination of naturally processed and presented vaccinia peptides.

TABLE 2

Conservation of the naturally processed and presented class I HLA-A*0201 vaccinia-derived peptide IVIEAIHTV among poxviruses causing infection in humans.

| Orthopox | GenBank Accession No. | Gene name | Protein ID | Protein Name |
|---|---|---|---|---|
| Vaccinia virus | | | | |
| Modified vaccinia Ankara (MVA) | U94848 | MVA161R | AAB96539.1 | thymidylate kinase (TmpK) |
| Copenhagen | M35027 | A48R | AAA48180.1 | CDS A48R, putative |
| Tian Tan | AF095689 | TA59R | AAF34060.1 | AAF34060.1 protein |
| Western Reserve (WR) | | VACWR174 | AAO89453.1 | TmpK |
| Variola major | | | | |
| Bangladesh-1975 | L22579 | J2R | AAA60903.1 | homolog of vaccinia virus CDS A48R (TmpK) |
| India-1967 | X69198 | J2R | CAA49101.1 | NA |
| Variola minor | | | | |
| Garcia-1966 | Y16780 | K2R | CAB54761.1 | K2R protein |
| Cowpox virus | | | | |
| Brighton Red | AF482758 | CPXV186 CDS | AAM13626.1 | CPXV186 protein |
| Monkeypox | | | | |
| Zaire-96-I-16 | AF380138 | A49R | AAL40617.1 | similar to Copenhagen A48R |
| Camelpox | | | | |
| Camelpox M-96 (Kazakhstan) | AF438165 | 156596 ... 157279 CDS | AAL73876.1 | TmpK |

Conclusion

We have used accurate mass measurement of the precursor ion in conjunction with tandem mass spectrometry to identify a novel HLA class I peptide from a vaccinia protein that is presented after infection of B-cells with live vaccinia virus. The MS/MS data, in conjunction with accurate mass data for the precursor ion, identifies the peptide as IVIEAIHTV (SEQ ID NO: 1) from the thymidylate kinase protein of vaccinia virus. The combination of 2D-LC for peptide separation, with tandem mass spectrometry and precursor ion accurate mass data is a powerful tool for identifying naturally processed peptides presented by the HLA pathway. In the examples reported here for naturally processed peptides lacking the C-terminal amino acid restraints of a tryptic or Lys-C generated peptide, accurate mass has been used to both augment fragmentation data and as a means of discovering false positives from database search results.

Example 2

Peptide-based Vaccine Comprising Vaccinia Epitope (Prophetic)

The Vaccinia virus peptide (SEQ ID NO:1 or $X_1$-SEQ ID NO:1-$X_2$) is isolated and purified as described above and used in a peptide-based vaccine. The peptide, either alone or in combination with other Vaccinia virus peptides, could be used in a peptide-based vaccine to protect against smallpox or other Orthopoxvirus infection. The peptide logically could and will be used in the directed design of newer smallpox vaccines. The major advantage of such an approach includes avoidance of the safety problems and contraindications present for any live viral vaccine (i.e. there are a large number of persons who cannot safely receive a live viral vaccine, such as a highly immunocompromised person), and the ease and lower cost of manufacturing such a vaccine.

Creation of a peptide-based vaccine is well known to a skilled artisan. One of skill in the art should review the following references for exemplary models of peptide or peptide-like vaccines. See Halassy B, et al., "Immunogenicity of peptides of measles virus origin and influence of adjuvants," Vaccine 24:185-194 (2006); Crowe S, et al., "Identification of protective and non-protective T cell epitopes in influenza," Vaccine 24:452-456 (2006); Francis J & Larché M, "Peptide-based vaccination: where do we stand?," Curr. Opin. Allergy Clin. Immunol. 5:537-343 (2005); Halassy B, "Immunogenicity of peptides of measles virus origin and influence of adjuvants," Vaccine 24:185-194 (2006); Pashine A, et al., "Targeting the innate immune response with improved vaccine adjuvants," Nat. Med. 11:S63-68 (2005); Holmgren J & Czerkinsky C, "Mucosal immunity and vaccines," Nat. Med. 11:S45-53 (2005); Robinson J & Amara R, "T cell vaccines for microbial infections," Nat. Med. 11:S25-32 (2005); Plotkin S, "Vaccines: past, present and future," Nat. Med. 11:S5-11 (2005); BenMohamed L, et al., "Lipopeptide vaccines—yesterday, today, and tomorrow," Lancet Infect. Dis. 2:425-431 (2002); Torrens I, et al., "Immunotherapy with CTL peptide and VSSP eradicated established human papillomavirus (HPV) type 16 E7-expressing tumors," Vaccine 23:5768-5774 (2005); Roberts J, et al., "Phase 2 study of the g209-2M melanoma peptide vaccine and low-dose interleukin-2 in advanced melanoma: Cancer and Leukemia Group B 509901," J. Immunother. 29:95-101 (2006); Diamond D, et al., "Development of a candidate HLA A*0201 restricted peptide-based vaccine against human cytomegalovirus infection," Blood 90:1751-1767 (1997); La Rosa C, et al., "Preclinical development of an adjuvant-free peptide vaccine with activity against CMV pp65 in HLA transgenic mice," Blood 100:3681-3689 (2002); Pialoux G, et al., "Lipopeptides induce cell-mediated anti-HIV immune responses in seronegative volunteers," AIDS 15:1239-1249 (2001); Livingston B, et al., "The hepatitis B virus-specific CTL responses induced in humans by lipopeptide vaccination are comparable to those elicited by acute viral infection," J. Immunol. 159:1383-1392 (1997); Vitiello A, et al., "Development of a lipopeptide-based therapeutic vaccine to treat chronic HBV infection. I. Induction of a primary cytotoxic T lymphocyte response in humans," J. Clin. Invest. 95:341-349 (1995); Fonseca D, et al., "Evaluation of T-cell responses to peptides and lipopeptides with MHC class I binding motifs derived from the amino acid sequence of the 19-kDa lipoprotein of Mycobacterium tuberculosis," Mol. Immunol. 37:413-422 (2000); BenMohamed L, et al., "High immunogenicity in chimpanzees of peptides and lipopeptides derived from four new Plasmodium falciparum pre-erythrocytic molecules," Vaccine 18:2843-2855 (2000); and Oseroff C, et al., "HLA class I-restricted responses to vaccinia recognize a broad array of proteins mainly involved in virulence and viral gene regulation," Proc. Natl. Acad. Sci. USA 102:13980-13985 (2005), each of which is incorporated herein by reference as if set forth in its entirety.

The effectiveness of such a peptide-based vaccine is easily measured in non-human primate and smaller animal studies. After optimization of the route and dose of peptide-based vaccine, animals that have and have not been immunized are exposed to sub-lethal and lethal doses of wild Vaccinia virus. Efficacy can be defined in multiple ways including lack of evidence of infection, lack of serious consequences to infection and survival after wild virus infection.

Example 3

Diagnostic Assay Comprising Vaccinia Epitope (Prophetic)

The Vaccinia virus peptide (SEQ ID NO:1) is isolated and purified as described above and used in a diagnostic assay.

SEQ ID NO:1, either alone or in combination with other Vaccinia virus peptides, could be used in diagnostic assays designed to determine whether Vaccinia virus or another Orthopoxvirus is present. One would preferably wish to analyze a biological sample taken from a human patient and detect the presence or absence of SEQ ID NO:1 by means of specific antibodies or other probes. Direct detection of SEQ ID NO:1 is possible as a diagnostic modality proving the presence of recent virus either within a blood sample or potentially directly within a tissue specimen.

In addition, because SEQ ID NO:1 derives directly from Vaccinia virus, antibody to the peptide unambiguously reflects the presence and/or previous exposure to either wild Vaccinia virus or an Orthopoxvirus. In the case of someone not previously immunized, the presence of IgM and/or IgG antibody to the peptide can only be attributed to infection with Vaccinia virus or an Orthopoxvirus. In the case of someone previously immunized against smallpox, an anamnestic (or long-term memory) immune response, measured by detection of IgM antibody to these peptides, is attributed to re-exposure and re-infection by wild Vaccinia virus or Orthopoxvirus; while detection of IgG indicates the presence of protective antibody.

SEQ ID NO:1 could be directly incorporated onto plastic wells for use in an ELISA antibody assay, into microparticles in an ELISA or luminex technology assay, or even more generically into an ELISPOT assay. Conversely, it would also be possible to make monoclonal antibodies against SEQ ID NO:1, then make animal anti-human anti-Vaccinia virus peptides to these antibodies and use this in a biologic assay for the presence of antibody to SEQ ID NO:1. Thus, SEQ ID NO:1 will ultimately be utilized in the design of subunit antibody assays to these specific vaccinia-derived peptides. It is important to note that the value of this approach may be the fine dissection of the immune response to an otherwise large virus. This assumes particular relevance when one considers that these peptides are, in fact, the most prevalent Vaccinia virus-derived peptides as evidenced by the fact that these were found in high abundance on antigen-presenting cells by our methodology.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth by the appended claims.

We claim:

1. An isolated peptide, wherein the peptide consists of $X_1$-SEQ ID NO:1-$X_2$, wherein $X_1$ and $X_2$ are amino acid segments of 0-11 amino acids in length.

2. The peptide of claim 1 wherein $X_1$ and $X_2$ comprise naturally occurring contiguous thymidylate kinase sequence.

3. The peptide of claim 1 wherein the peptide is 20 amino acids or less.

4. The peptide of claim 1 wherein the peptide is 12 ammo acids or less.

5. The peptide of claim 1 wherein either $X_1$ or $X_2$ is equal to zero.

6. The peptide of claim 1 wherein the peptide is chemically synthesized.

7. The peptide of claim 1 wherein both $X_1$ and $X_2$ are equal to zero.

* * * * *

UNITED STATES PATENT AND TRADEMARK OFFICE
CERTIFICATE OF CORRECTION

PATENT NO. : 7,622,120 B2  Page 1 of 1
APPLICATION NO. : 11/738210
DATED : November 24, 2009
INVENTOR(S) : Poland et al.

It is certified that error appears in the above-identified patent and that said Letters Patent is hereby corrected as shown below:

Column 16, line 30 "fme" should be --fine--

Column 19, claim 4 "ammo" should be --amino--

Signed and Sealed this

Eleventh Day of May, 2010

David J. Kappos
*Director of the United States Patent and Trademark Office*

SEQUENCE LISTING

```
<160> NUMBER OF SEQ ID NOS: 10

<210> SEQ ID NO 1
<211> LENGTH: 9
<212> TYPE: PRT
<213> ORGANISM: Vaccinia virus

<400> SEQUENCE: 1

Ile Val Ile Glu Ala Ile His Thr Val
1               5

<210> SEQ ID NO 2
<211> LENGTH: 9
<212> TYPE: PRT
<213> ORGANISM: Vaccinia virus

<400> SEQUENCE: 2
```

```
Ile Val Leu Glu Ala Ile Ala Glu His
1               5

<210> SEQ ID NO 3
<211> LENGTH: 9
<212> TYPE: PRT
<213> ORGANISM: Vaccinia virus

<400> SEQUENCE: 3

Ile Val Leu Glu Ser Pro Ser His Ile
1               5

<210> SEQ ID NO 4
<211> LENGTH: 9
<212> TYPE: PRT
<213> ORGANISM: Vaccinia virus

<400> SEQUENCE: 4

Ile Val Ile Glu Ser Pro Ile His Ser
1               5

<210> SEQ ID NO 5
<211> LENGTH: 9
<212> TYPE: PRT
<213> ORGANISM: Vaccinia virus

<400> SEQUENCE: 5

Ile Val Leu Glu Leu Ala Cys Tyr Ala
1               5

<210> SEQ ID NO 6
<211> LENGTH: 9
<212> TYPE: PRT
<213> ORGANISM: Vaccinia virus

<400> SEQUENCE: 6

Leu Val Leu Glu Val Asn Asn Pro Pro
1               5

<210> SEQ ID NO 7
<211> LENGTH: 9
<212> TYPE: PRT
<213> ORGANISM: Vaccinia virus

<400> SEQUENCE: 7

Leu Val Leu Glu Leu Leu Thr His Gly
1               5

<210> SEQ ID NO 8
<211> LENGTH: 9
<212> TYPE: PRT
<213> ORGANISM: Vaccinia virus

<400> SEQUENCE: 8

Leu Val Ile Asp Val Glu Leu Pro Pro
1               5

<210> SEQ ID NO 9
<211> LENGTH: 9
<212> TYPE: PRT
<213> ORGANISM: Vaccinia virus

<400> SEQUENCE: 9

Leu Val Leu Asp Val Glu Ile His Gly
```

-continued

```
1               5

<210> SEQ ID NO 10
<211> LENGTH: 9
<212> TYPE: PRT
<213> ORGANISM: Vaccinia virus

<400> SEQUENCE: 10

Leu Val Leu Thr Leu Val Leu Ser His
1               5
```